United States Patent
Berner (10) Patent No.: US 9,910,255 B2
(45) Date of Patent: Mar. 6, 2018

(54) OPTICAL SYSTEM FOR GENERATING A PATTERN WHICH CHANGES OVER TIME FOR A CONFOCAL MICROSCOPE

(71) Applicant: Sirona Dental Systems GmbH, Bensheim (DE)

(72) Inventor: Markus Berner, Bulach (CH)

(73) Assignee: Dentsply Sirona, Inc., York, PA (US)

( * ) Notice: Subject to any disclaimer, the term of this patent is extended or adjusted under 35 U.S.C. 154(b) by 0 days.

(21) Appl. No.: 15/021,588

(22) PCT Filed: Sep. 11, 2014

(86) PCT No.: PCT/EP2014/069365
§ 371 (c)(1),
(2) Date: Mar. 11, 2016

(87) PCT Pub. No.: WO2015/036467
PCT Pub. Date: Mar. 19, 2015

(65) Prior Publication Data
US 2016/0231551 A1    Aug. 11, 2016

(30) Foreign Application Priority Data
Sep. 11, 2013    (DE) .................. 10 2013 218 231

(51) Int. Cl.
G02B 21/00    (2006.01)
G02B 27/10    (2006.01)
(Continued)

(52) U.S. Cl.
CPC .......... *G02B 21/0032* (2013.01); *A61C 9/006* (2013.01); *G02B 21/004* (2013.01);
(Continued)

(58) Field of Classification Search
CPC ............ G02B 21/0004; G02B 21/0012; G02B 21/0016; G02B 21/002; G02B 21/0024;
(Continued)

(56) References Cited

U.S. PATENT DOCUMENTS 3,897,136 A    7/1975  Bryngdahl
5,218,195 A *  6/1993  Hakamata .............. B82Y 15/00
                                                250/216
(Continued)

FOREIGN PATENT DOCUMENTS

CN      101680749 A      3/2010
DE   10 2010 047 353 A1  4/2012
(Continued)

OTHER PUBLICATIONS

Mar. 4, 2015 International Search Report, International Application No. PCT/EP2014/069365.
(Continued)

*Primary Examiner* — Loha Ben
(74) *Attorney, Agent, or Firm* — Fitzpatrick, Cella, Harper & Scinto (57) ABSTRACT

The invention relates to an optical system for generating a pattern which changes over time for a confocal microscope. The system includes a light source arrangement, a beam splitter, and a lens arrangement. The beam splitter allows for passage of a light beam proceeding from the light source arrangement in the direction of an object and for deflecting the reflected light beam, reflected by the object in a focal plane, in the direction of a detector. The detector includes a detector pattern for detecting an image of the object. The lens arrangement is between the beam splitter and the object and includes: a light source that generates the light beam, and a device configured to switch a direction of polarization of the light beam to generate a changing projector pattern.

18 Claims, 8 Drawing Sheets (51) Int. Cl.
*A61C 9/00* (2006.01)
*G02F 1/01* (2006.01)
*G02B 21/36* (2006.01)
*G02F 1/03* (2006.01)
*A61B 5/00* (2006.01)
*A61B 5/107* (2006.01)
*G02B 5/30* (2006.01)

(52) U.S. Cl.
CPC ....... *G02B 21/008* (2013.01); *G02B 21/0028* (2013.01); *G02B 21/0092* (2013.01); *G02B 21/367* (2013.01); *G02B 27/10* (2013.01); *G02F 1/0136* (2013.01); *G02F 1/0311* (2013.01); *A61B 5/0066* (2013.01); *A61B 5/0068* (2013.01); *A61B 5/1077* (2013.01); *G02B 5/3083* (2013.01); *G02B 21/365* (2013.01); *G02F 1/03* (2013.01)

(58) Field of Classification Search
CPC ............ G02B 21/0028; G02B 21/0032; G02B 21/0036; G02B 21/0068; G02B 21/008; G02B 21/004; G02B 21/0092; G02B 21/361; G02B 21/365–21/368; G02B 5/3025; G02B 5/3083; G02B 27/10; A61C 9/006; G02F 1/0136; G02F 1/03; G02F 1/0311; A61B 5/0066; A61B 5/0068; A61B 5/1077
USPC ....... 359/245, 246, 251–253, 257, 386, 389, 359/393; 250/201.5, 216, 225, 234; 348/46
See application file for complete search history.

(56) References Cited

U.S. PATENT DOCUMENTS

| | | | | |
|---|---|---|---|---|
| 5,659,384 A * | 8/1997 | Ina | ................... | G02B 21/0016 355/53 |
| 6,043,932 A * | 3/2000 | Kusunose | ............ | G02B 21/002 359/368 |
| 6,195,202 B1 * | 2/2001 | Kusunose | ............ | G02B 21/002 359/204.1 |
| 6,437,319 B1 * | 8/2002 | Hashimoto | .......... | G11B 7/1381 250/201.5 |
| 6,525,875 B1 * | 2/2003 | Lauer | ................... | G03H 1/0443 359/368 |
| 7,808,701 B2 | 10/2010 | Ouchi | | |
| 7,852,492 B2 | 12/2010 | Berner | | |
| 7,977,625 B2 | 7/2011 | Schwertner | | |
| 8,570,530 B2 | 10/2013 | Liang | | |
| 8,878,905 B2 * | 11/2014 | Fisker | ................. | A61B 5/0068 348/46 |
| 8,937,723 B2 * | 1/2015 | Cenko | ................. | A61B 5/0066 356/479 |
| 2004/0190134 A1 | 9/2004 | Tahara et al. | | |
| 2007/0109559 A1 | 5/2007 | Babayoff et al. | | |
| 2011/0141483 A1 | 6/2011 | Lee et al. | | |
| 2012/0268812 A1 | 10/2012 | Anhut et al. | | |
| 2013/0182306 A1 | 7/2013 | Anhut et al. | | |

FOREIGN PATENT DOCUMENTS

| | | |
|---|---|---|
| DE | 10 2011 013 613 A1 | 4/2012 |
| EP | 2 051 042 A1 | 4/2009 |
| EP | 2 136 233 A1 | 12/2009 |
| EP | 2 258 254 A1 | 8/2010 |
| WO | 2011/139150 A1 | 11/2011 |
| WO | 2013/105922 A2 | 7/2013 |

OTHER PUBLICATIONS

Written Opinion of the International Search Authority dated Sep. 11, 2013, in PCT/EP2014/069365.
Office Action dated Nov. 7, 2014, in German Patent Application No. 10 2013 218 231.7.
Office Action dated Oct. 10, 2017, issued in Chinese Patent Application No. 201480050305.1.

* cited by examiner

OPTICAL SYSTEM FOR GENERATING A PATTERN WHICH CHANGES OVER TIME FOR A CONFOCAL MICROSCOPE

TECHNICAL FIELD

The invention relates to an optical system for generating a pattern which changes over time for a confocal microscope.

PRIOR ART

There are various types of confocal microscopes that detect a surface of an object to be scanned based on the fact that the surface is in focus. Examples of such systems are laser confocal microscopes, such as are known from US2007/0109559 A1, or pOFPT (=parallel Focal Point Optical Tomography), as described in the Swiss patent application 016247/07.

In a pOFPT scanner, a moving pattern is projected onto an object to be scanned. This is advantageous because it is a simpler and more accurate signal technology to detect changing patterns than static ones. This movement is realized there such that a mask with the pattern is mechanically moved quickly. The movement is oscillating or continuous.

However, this mechanical motion has some significant disadvantages. The mechanism requires space, which makes a compact design impossible. The mechanism is also relatively expensive. In addition, the mechanical movement is not entirely precise. In particular, the accuracy of the rate of change is limited, which substantially increases the cost of the analysis. It can even cause operational failures in the mechanical movement.

There are optical elements that would allow a movement or change of the pattern. These elements are used, for example, in projectors. However, they are too slow for the desired scan. For example, the LCDs for LCD projectors allow a maximum of 200 image changes per second. However, for an application with scanning using the system described here, at least 2,000 image changes per second are necessary, but 20,000 are even better.

It is therefore the object of the present invention to provide an optical system for a confocal microscope and an associated method in which a moving or changing of the pattern in particular is simplified, and the change is very precisely time-controlled and can be exactly synchronized with the subsequent evaluation of the signals.

DESCRIPTION OF THE INVENTION

This object is achieved by an optical system and method as set forth in the claims. Advantageous developments of the invention are specified in the dependent claims.

According to the invention, an optical system for a confocal microscope is provided comprising a light source arrangement from which light beams travel to an object that reflects the light beams, a beam splitter for allowing passage of the light beams proceeding from the light source arrangement in the direction of the object and for deflecting light beams reflected by the object in a focal plane in the direction of a detector with a detector pattern for detecting an image of the object and a lens arrangement between the beam splitter and the object. In particular, the light source arrangement has at least one light source and a device that switches the direction of polarization of the light beams emitted by the at least one light source to generate a changing projector pattern without moving a mask having the projector pattern.

Preferably, the beam splitter is a polarizing beam splitter. Therefore, the light of the movable projector pattern should always have the same polarization direction.

According to the invention, the mechanical movement is thus replaced by a fixed, special optical arrangement and at least one polarized light source, in which the polarization direction is changed. The projected pattern or projector pattern then changes as fast as the polarization direction of the light source arrangement changes. The change in the polarization direction can be carried out as quickly as desired.

Preferably, the device for switching the light beams emitted by the at least one light source is fixedly arranged downstream with respect to their polarization direction of the light source, and a controllable optical retarder, which switches the polarization direction between two different polarization directions. A fast switching and a change in the polarization direction is thus possible.

The controllable optical retarder is preferably a Pockels cell that rotates the polarization direction, depending on the voltage applied to electrical terminals, from entrance to exit, the voltage being switched between two voltages V1 and V2 in such a way that the retardation changes by lambda/2 or an odd multiple thereof. Fast and well-controlled switching is possible.

Alternatively, the controllable optical retarder is preferably a stationary rotating lambda/4 retarder. Fast and simple switching can also be realized using such a lambda/4 retarder.

Alternatively, the light source arrangement preferably has two light sources and a switching device as a device for switching the light beams emitted by the at least one light source with respect to its direction of polarization, the light paths of the two light sources being combined into a single light path, the two light sources emitting polarized light and the respective polarization directions of the two light sources being rotated 90°, and the switching device in each case switching only one of the light sources into an on state and thereby changing the respective polarization direction of the combined light.

The two light sources can be provided side by side in such close proximity that their light paths are combined into the single light path. A diffusion disk is preferably connected downstream of the light sources. Such a diffusion disk serves to better focus the incident light and radiate it in the desired direction.

The two light sources may be arranged offset by 90°, a beam combiner then combining their light paths into a single light path.

Through the above-described embodiments having two light sources and one switching device, a particularly accurate switching to a respective polarization direction is possible.

The respective light sources are preferably laser diodes which emit already naturally polarized light, or LEDs with downstream polarizers. Such light sources are to be used in a simple manner.

The light is preferably linearly polarized, and the two polarization directions are preferably rotated by 90° with respect to each other, so that simply structured polarization directions are used.

Preferably, a lambda/4 retarder downstream of the light source arrangement is provided that converts the polarization directions into two circular polarization directions, one counterclockwise and one clockwise. Due to this conversion of the polarization direction, a projector pattern can be generated in a simple manner.

Preferably provided between a structured retarder downstream of the lambda/4 retarder and the lens arrangement is a linear polarizer that blocks the light from positions at which the polarization is rotated 90°, and allows the light to pass through from positions at which the direction of polarization is present, so that the illumination pattern is transparent at these positions. This measure can also simplify the generation of a projector pattern, and it ensures that the light that goes toward the subsequent beam splitter always has the same polarization direction.

The illumination pattern or projector pattern is preferably a pattern that can be controlled as desired, a fixed line pattern or a fixed checkerboard pattern. These patterns are easy to use in practice.

Controllable patterns can be easily realized by employing a transparent LCD as used in LCD projectors. Creating a suitable image generates a structured retarder.

Preferably, means for aligning projector patterns and detector patterns are provided. The alignment of the pattern is necessary, so that a good image can be produced when the optical system is employed as a scanner.

As means for evaluating received signals, a filter is preferably provided whose switching frequency is synchronized with the switching frequency of the polarization direction of the light source. Preferably, the filter is realized as a lock-in amplifier. The synchronization serves to achieve an easily detectable signal during scanning.

Furthermore, the invention relates to a method of scanning using the optical system according to the invention for a confocal microscope and having the following steps: Aligning the projector pattern and the detector pattern, tuning the focal plane while the projector pattern is changed with a high switching frequency, obtaining a signal having a frequency corresponding to the switching frequency, narrow-band filtering of the received signal and searching for the maximum intensity of the signal after the narrow band filtering, and searching for a signal peak having a constant width.

Because of its compact design, the optical system according to the invention is especially well-suited for use in an intra-oral scanner for measuring teeth.

BRIEF DESCRIPTION OF THE DRAWINGS

The specified and other features and details of the invention will become clear to a person skilled in the art from the following detailed description and the accompanying drawings. The accompanying drawings illustrate features of the present invention based on an example, in which.

DETAIL DESCRIPTION OF THE PREFERRED EMBODIMENTS

Hereinafter, the present invention will be explained in detail based on preferred embodiments with reference to the figures.

Figure 1:
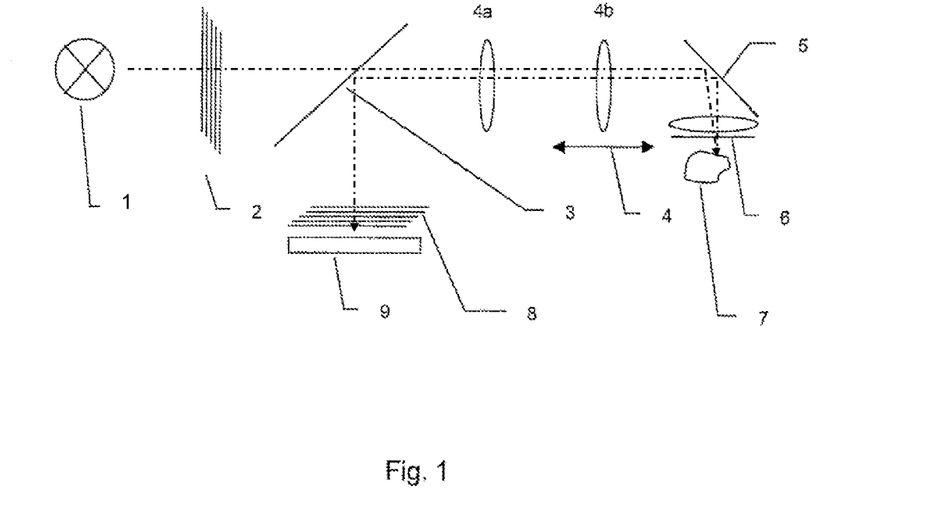
FIG. 1 shows a general structure of an optical system for a confocal microscope according to the present invention.

FIG. 1 shows the general structure of an optical system according to the invention for a confocal microscope, wherein a light source arrangement 1 is provided, and a projector pattern 2 is a projected pattern that changes depending on the polarization of the light source arrangement 1. The light source arrangement 1 in FIG. 1 is shown in detail in FIGS. 2 to 4 as a light source arrangement 1 with switchable polarization. Furthermore, a beam splitter 3 is provided which can be a polarizing beam splitter. In the case of a double arrow 4, a displacement of the focal plane is performed by moving the second lens 4b of a lens arrangement having a first lens 4a and a second lens 4b. Shown also are a reflecting mirror 5, a ¼ waveplate 6, an object 7 such as a tooth, a detector pattern 8 and a sensor 9. The detector pattern need not be used if the pixel pattern of the sensor is used as the detector pattern. The sensor may be, for example, a smart-pixel image sensor for pOCT.

Light beams from the projector pattern 2 run through the beam splitter 3 toward the object 7 through the first lens 4a and the second lens 4b up to a focal plane at the object 7. The light beams reflected by the object 7 run back through the lenses 4a and 4b and the beam splitter 3 toward the sensor 9 where an image of the object 7 is detected. In a laser confocal microscope, the illumination pattern or projector pattern comprises at least one point light source, the laser, and in a pOFPT device, the illumination pattern comprises an image transilluminated by a light source. The double arrow 4 at the second lens 4b indicates a movement of the second lens 4b, said movement resulting in a corresponding movement of the focal plane at the object 7. To move the second lens 4b, a drive device is provided which may be a controlled motor, for example.

Figure 2:
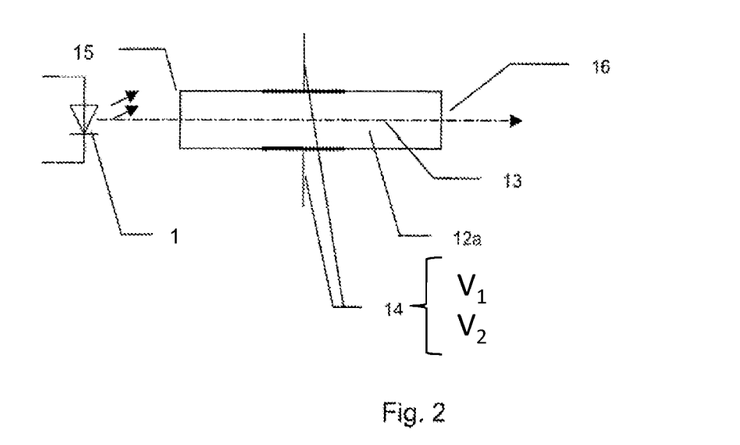
FIG. 2 shows a light source arrangement having a switchable polarization direction via a Pockels cell according to the present invention.

FIG. 2 shows a light source arrangement 1, 12a having a switchable polarization direction via a Pockels cell 12a with electrical connections 14, an optical beam path 13, a light entrance 15 and a light exit 16.

The light source 1 emits polarized light. It may, for example, be a laser diode which emits already naturally polarized light, or else an LED having a downstream polarizer. The Pockels cell 12a is a controllable optical retarder that can rotate the polarization direction, depending on the voltage applied to the electrical connections 14, from light entrance 15 to light exit 16.

The voltage is preferably switched between two voltages V1 and V2 that changes the delay by lambda/2 or an odd multiple thereof. Thus, the light at the light outlet 16 has two different polarization directions for the voltages V1 and V2, for example, two linearly polarized directions preferably rotated 90° or two circular polarization directions, one counterclockwise and one clockwise, or corresponding mixtures.

Figure 3:
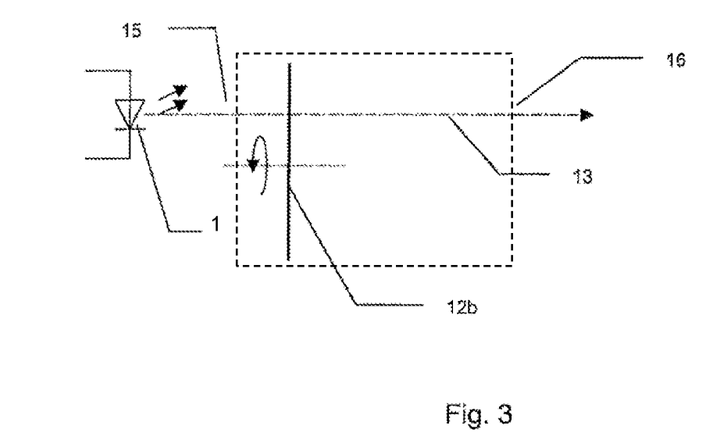
FIG. 3 shows a light source arrangement having a switchable polarization direction via (stationary rotating) waveplate according to the present invention.

FIG. 3 shows a light source arrangement comprising a light source 1 and a stationary rotating lambda/4 retarder 12b, an optical beam path 13, a light entrance 15 and a light exit 16. Instead of the Pockels cell 12a of FIG. 2, the delay and thus the polarization is changed at the light exit 16 by means of mechanical movement (in this case rotation) in a structure according to FIG. 3.

Figure 4:
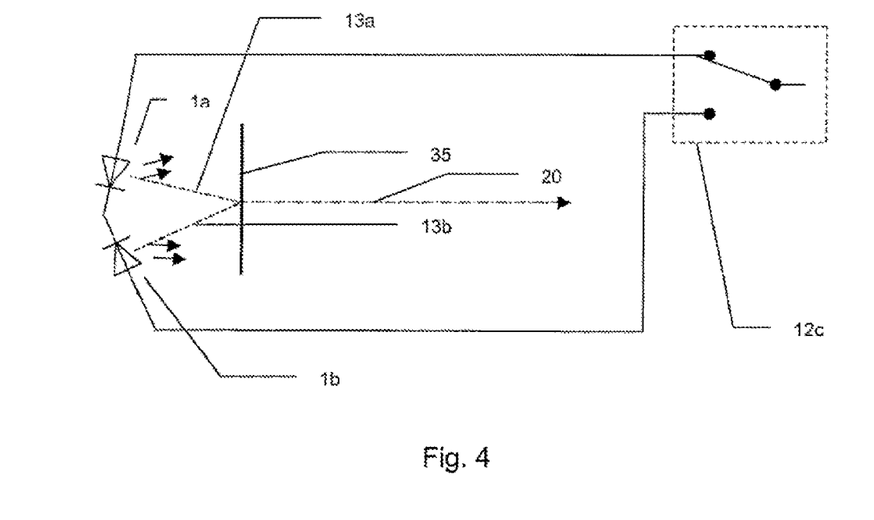
FIG. 4 shows a light source arrangement having a switchable polarization direction via two light sources according to the present invention.

FIG. 4 shows a light source arrangement comprising a first light source 1a and a second light source 1b. The two light sources 1a and 1b are arranged side by side. If they are arranged side by side very close to each other, an optical beam path 13a of the first light source 1a light path and an optical beam path 13b of the second light source 1b light path become an optical beam path 20 of the light path of the combined light paths of the first light source 1a and the second light source 1b.

The polarization direction of the combined light can now be switched via a switching device 12c by alternatively switching on only the light source 1a and only the light source 1b.

The two light sources 1a and 1b emit polarized light, and the respective polarization directions of the two light sources 1a and 1b are rotated 90°. The switching device 12c in each case switches only one of the light sources 1a and 1b into an on state and thereby changes the respective polarization direction of the combined light.

According to FIG. 4, a diffusion disk 35 is downstream of the light sources 1a and 1b to focus the light better and radiate it in the desired direction.

Figure 5:
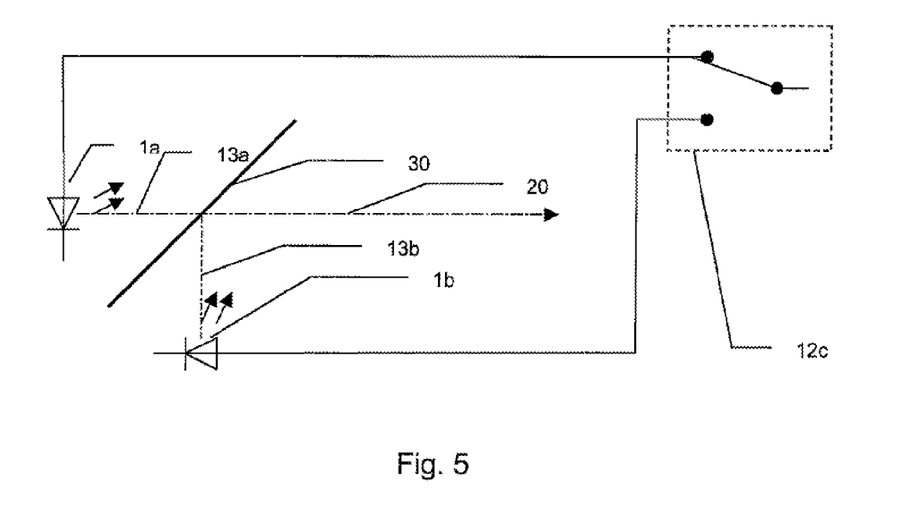
FIG. 5 shows another light source arrangement having a switchable polarization direction via two light sources according to the present invention.

FIG. 5 also shows a light source arrangement having a first light source 1a and a second light source 1b. The two light sources 1a and 1b are arranged offset by 90°, and a polarizing beam combiner/beam splitter 30 combines its light paths into a single light path. FIG. 5 further shows an optical beam path 13a of the light path of the first light source 1a, an optical beam path 13b of the light path of the second light source 1b, and an optical beam path 20 of the light path of the combined light paths of the first light source 1a and the second light source 1b.

In the embodiments of FIGS. 4 and 5, the light sources 1a and 1b emit polarized light. They can be, for example, laser diodes which emit already naturally polarized light, or an LED with a downstream polarizer. The two light sources 1a and 1b are configured in such a way that the polarization directions are rotated between them by 90°. According to the embodiment of FIG. 5, the beam combiner 30 combines the light paths 13a and 13b of the two light sources 1a and 1b into a single light path 20. According to the embodiment of FIG. 4, the single light path 20 is produced by arranging the two light sources 1a and 1b side by side very close to each other. The bundling and alignment can be improved by providing the depicted diffusion disk.

The polarization direction of the combined light can now be switched via the switching device 12c by alternatively switching on only the light source 1a and only the light source 1b.

In this arrangement, the light is linearly polarized, and the two polarization directions are rotated 90° with respect to each other. If required, by connecting a lambda/4 retarder downstream, the polarization directions can be converted into two circular polarization directions, one counterclockwise and one clockwise.

Using a structured retarder and a linear polarizer downstream can generate an alternating pattern; one pattern or the other is projected depending on the polarization direction of the illumination unit.

Figure 6:
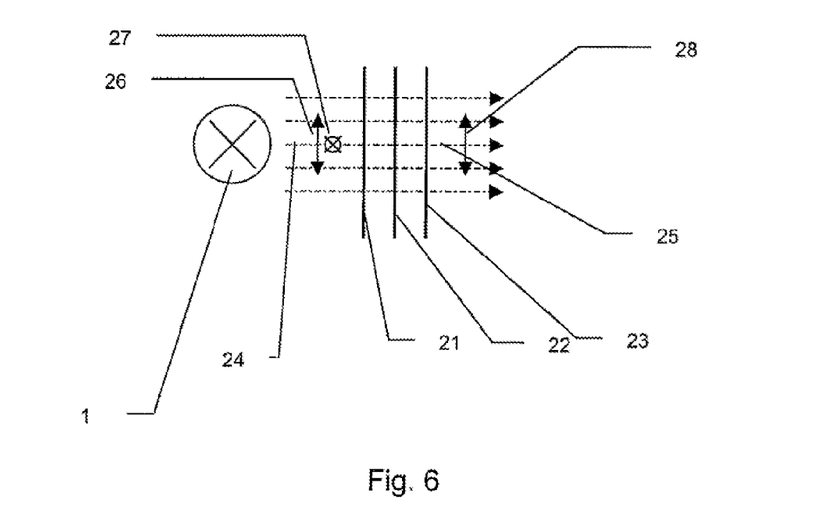
FIG. 6 shows an arrangement for generating an alternating stripe pattern according to the present invention.

FIG. 6 shows an arrangement for generating an alternating stripe pattern, in which are shown in particular: a light source 1, an unpatterned lambda/4 retarder 21, a structured retarder 22, a linear polarizer 23, light 24 from the source, light 25 with a switching pattern, a first polarization direction 26 of light source 1, a second polarization direction 27 of the light source and a polarization direction 28 of the light with the pattern.

The light source 1 emits light with a changing polarization direction 26, 27, such as linearly polarized light. The lambda/4 retarder 21 converts linearly polarized light into circular polarized light, switching between clockwise and counterclockwise. The structured retarder 22 is structured in such a way that it is retarded at certain positions by +lambda/4 and at other positions by −lambda/4.

The light from light source 1 at certain positions therefore undergoes a delay by lambda/2, namely +lambda/4 from the retarder 21 and +lambda/4 from the structured retarder 22, and at other positions there is no delay, namely +lambda/4 from the retarder 21 and −lambda/4 from the structured retarder 22.

At the positions at which the light undergoes a delay of lambda/2, the polarization direction is rotated by 90°. At the other positions, it is not rotated.

If light source 1 is then switched in such a way that the polarization direction 26 is present, those positions of the pattern are transparent at which no rotation of the polarization takes place. The light from the positions at which the polarization is rotated by 90° is blocked at the linear polarizer 23. Conversely, if the light source 1 is switched so that the polarization direction 27 is present, then the other positions of the pattern are transparent.

The arrangement of FIG. 6 is a possible and logical arrangement for generating a suitable projector pattern. However, the delay may also be distributed in other ways, and the unstructured lambda/4 retarder 21 is not always necessary, and it can also be arranged between elements 22 and 23.

However, it is important that the differences between the delays at the structured retarder 22 be at least approximately lambda/2 or an odd multiple thereof, so that linearly polarized light having a polarization direction rotated 90° is present upstream of the linear polarizer 23.

Figure 7:
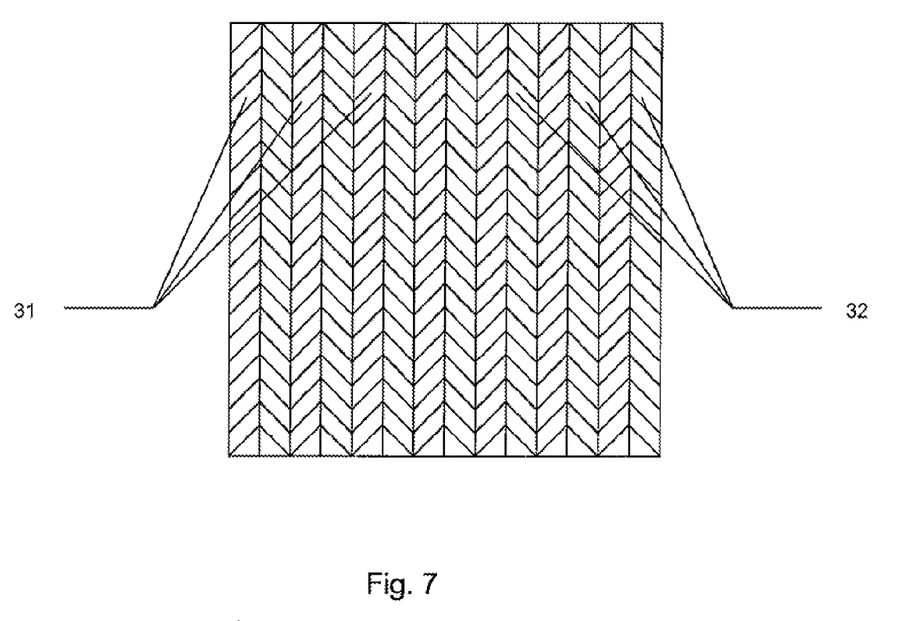
FIG. 7 shows a structured retarder according to the present invention.

To generate a switching stripe pattern as a projector pattern, for example through the arrangement shown in FIG. 5, the patterned retarder appears, for example, as it is shown in FIG. 7. In FIG. 7, points with +lambda/4 delay 31 and points with −lambda/4 delay 32 can be seen.

Such structured retarders are now state-of-the-art and are used, for example, in 3D televisions. It is also possible to use a transparent LCD such as is used, for example, in projectors. This is also a structured retarder in which the zones can be switched with the delay corresponding to the image on the LCD. The structured retarder may have any pattern. Suitable patterns for the use according to the invention are, for example, line or checkerboard patterns.

Figure 8:
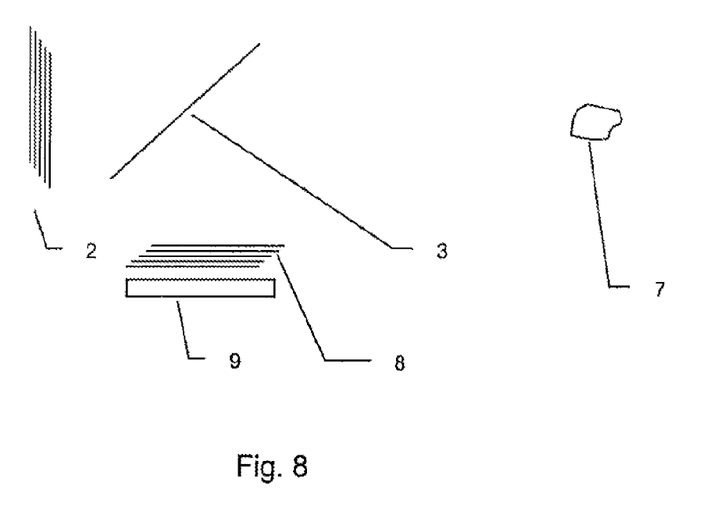
FIG. 8 is an illustration for positioning the changing pattern.

To achieve a good signal when using the optical system according to the invention, the projector pattern and detector pattern of the system must be aligned and positioned accordingly. Such a positioning of the changing pattern will now be described with reference to FIG. 8. In FIG. 8, a projector pattern 2 is to be seen as a projected pattern that changes as a function of the polarization of the light source. Also shown are a detector pattern 8 which must not be used when the pixel pattern of the sensor is used as a detector pattern, a sensor 9 which may be a smart pixel image sensor for pOCT, a beam splitter 3 which may be a polarizing beam splitter, and a measurement object 7.

Seen from the measurement object 7, the projector pattern 2 and the detector pattern 8 must be optically arranged at the same location. The projector pattern 2 sees the object directly, and the detector pattern 8 sees the object through the beam splitter 3. But both patterns appear in the same place.

It should be noted that the arrangement of projector pattern 2 and detector pattern 8 can be reversed. In the following, the reference is always to detector pattern 8, even if no such component need be used. Ideally, the pixel structure of the sensor is used directly as a detector pattern.

Figure 9:
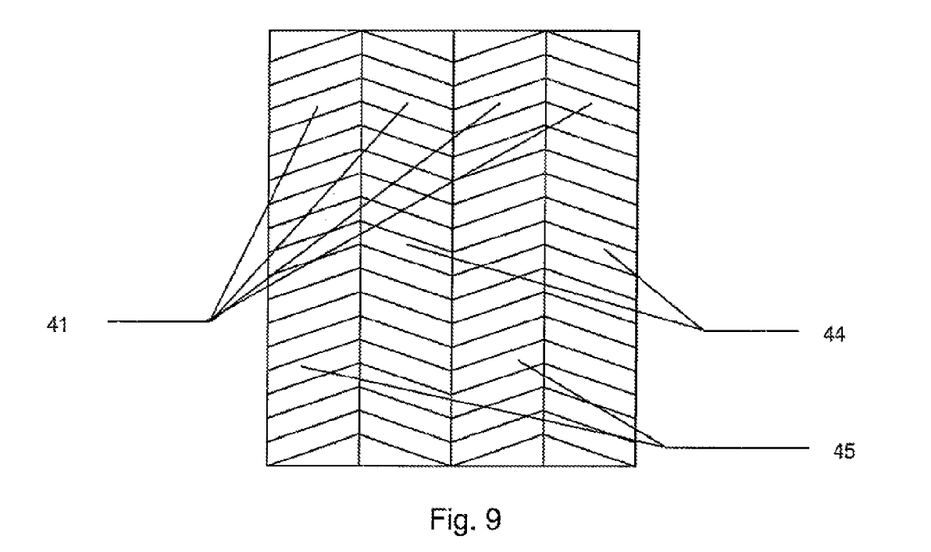
FIG. 9 shows a projector pattern.
Figure 10:
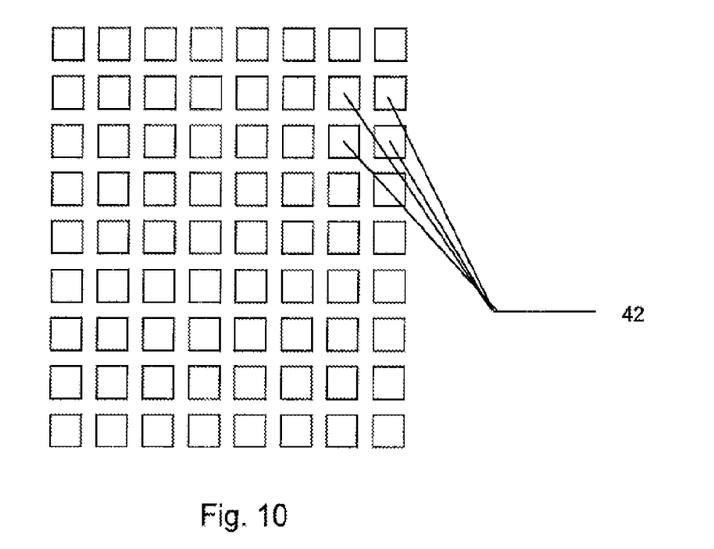
FIG. 10 shows a detector pattern.

There now follows a description of a lateral alignment of the projector pattern and detector pattern. In the following example, the projector pattern is a stripe pattern, and the detector pattern is the pixel structure of an image sensor, as can be seen in FIGS. 9 and 10. Here, a projector pattern 41 is a stripe pattern, and a detector pattern 42 is a pixel pattern of an image sensor. Shown also are a first area type 44 which is bright if a polarization of the source 1 is in a first state and dark if the polarization is in a second state, and a second area type 45 which is bright if a polarization of source 1 is in the second state and dark if the polarization in the first state.

Figure 11:
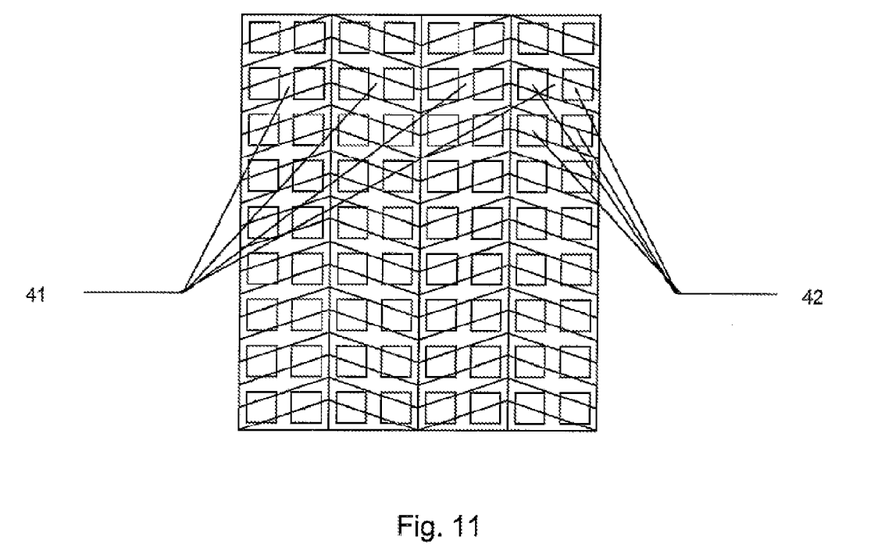
FIG. 11 shows a projector pattern and a detector pattern seen from the measurement object having a correct orientation.
Figure 12:
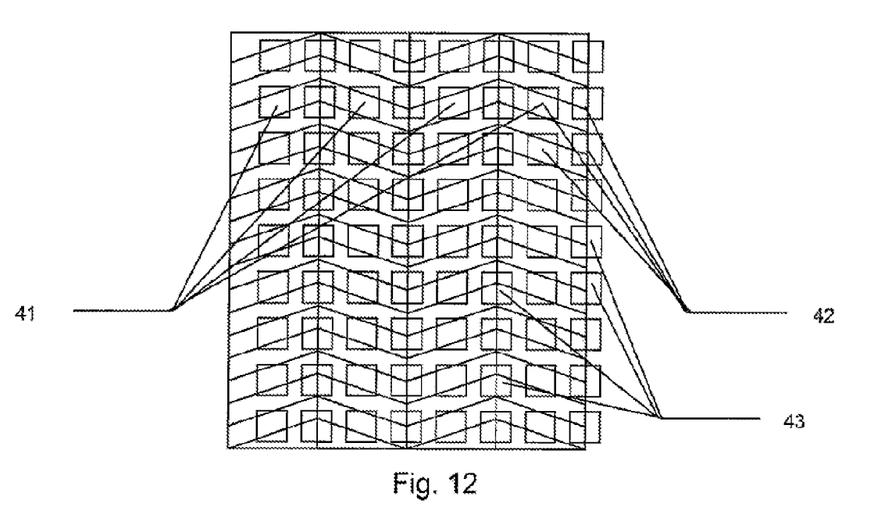
FIG. 12 shows a projector pattern and a detector pattern seen from the measurement object having an incorrect orientation.

FIG. 11 now shows a projector pattern and a detector pattern seen from the measurement object with correct alignment, and FIG. 12 shows a projector pattern and a detector pattern seen from the measurement object with misalignment.

Also shown in FIGS. 11 and 12—in addition to the projector pattern 41 as a stripe pattern, the detector pattern 42 as a pixel pattern of an image sensor, the first area type 44 and the second area type 45 of FIGS. 9 and 10—are pixels 43, which will supply no signal.

When aligned correctly, as can be seen in FIG. 11, all detector pixels will provide a signal. In the case of faulty alignment as can be seen in FIG. 12, such detector pixels 43 which are in a transition of the projector pattern, provide no signal or only a weak signal.

The lateral (side) mutual alignment can be simplified in certain cases. If e.g. a LCD display having a pixel pattern which is finer than the structure of the detector pattern is used for the projector pattern, the position of the pattern can be adapted by means of software to the position of the detector pattern. If a detector pattern is used having a structure that is finer than the required lateral resolution, such as a high-resolution image sensor, an alignment can be omitted by eliminating the pixels that deliver too weak a signal.

A description of the evaluation of the signal follows. In the following description, it is assumed that a light source $1a$ and a light source $1b$ are used as shown in FIG. 5. However, with appropriate adjustments, the description also applies to other arrangements of FIGS. 2 to 4.

The scanning with the scanner is done then as follows: The position of the focal plane is tuned. During the tuning, the polarization of the light source is continuously switched, such as with a frequency f1. If the object to be scanned is far enough away from the focal plane of the projector pattern, a single detector pixel sees the projector pattern so unfocused that the same amount of light from the two surface types 44 and 45 of FIG. 8 strikes the pixel. The two light sources $1a$ and $1b$ of the illumination unit are adjusted, for example by application of current, in such a way that the measured amount of light is then actually equal.

If the object to be scanned is in the focal plane of the projector pattern, differences in intensity strike each pixel depending on whether the surface type 44 or 45 is in fact bright.

Figure 13:
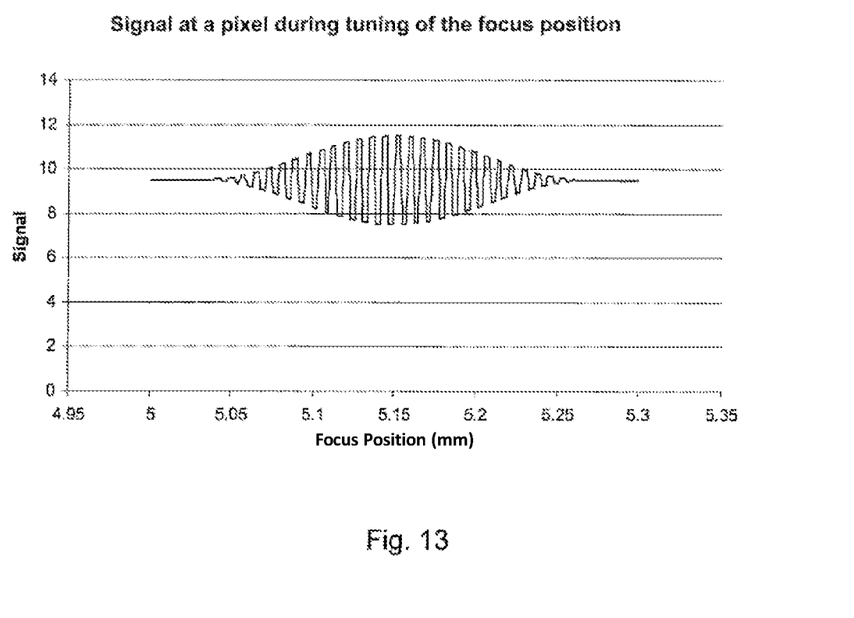
FIG. 13 shows a signal at a pixel during tuning of the focus position.

The signal then appears at a pixel somewhat as is shown in FIG. 13.

In the example of FIG. 13, there is an object at the position of the corresponding pixel at 5.15 mm. The frequency of the signal corresponds to the frequency f1 with which the polarization of the light source is switched.

To find the position where the object is located, the following procedure is followed: Narrow band filtering of the signal is performed at the frequency f1, and the maximum intensity of the signal after the narrow band filtering is searched.

Preferably, the switching frequency is relatively high, so many periods of the alternating signal occur for the surface. This allows a very narrow-band filtering of the alternating signal, thereby also filtering out noise and hum of the signal.

The filtering is ideally realized as a digital filter, the switching frequency of the filter being exactly synchronized with the switching of the polarization direction of the source. For this purpose, a lock-in amplifier is ideally used.

Through conscious asymmetries in the filtering, asymmetries can thus also be compensated in the illumination unit as needed: If the signal is not exactly the same strength in the two polarization directions, a certain alternating signal results even at a distance from the focus. This can be corrected by the light levels being adjusted relative to each other, or else by targeted asymmetrically filtering.

This narrow-band filtering is done ideally using smart pixel sensors for OCT (OCT=Optical Coherence Tomography) applications. In that context, this filtering is performed for each pixel on the sensor.

Figure 14:
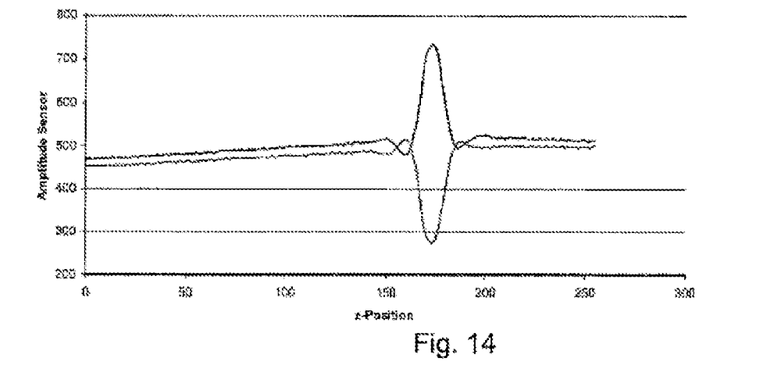
FIG. 14 shows a resulting signal at a pixel after a narrow-band filtering.

The resulting signal at a pixel after narrow band filtering then looks like it appears in FIG. 14.

The z-position is a measure of the position of the focal plane. Located at the position of the local maximum or minimum is the surface for the corresponding pixel.

Figure 15:
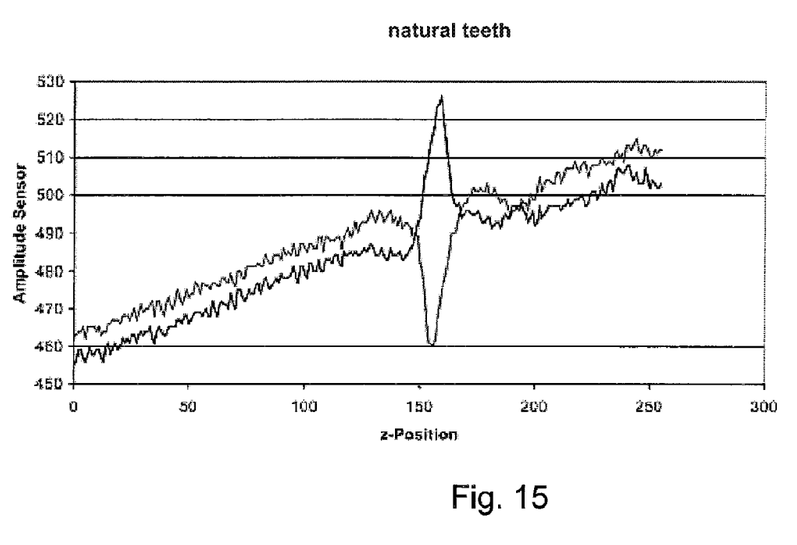
FIG. 15 shows a resulting signal at a pixel after a narrow-band filtering for a scan of natural teeth.

Less cooperative surfaces, such as the material of natural teeth, produce a similar, although weaker signal, as can be seen in FIG. 15.

Ideally, the signal regarding the Z position would be constant and would have a maximum or minimum only at the point at which the pattern is sharply projected onto the object. In practice, the signal is not really constant in any focal region. The reasons for this are noise superimposed on the signal and drift of the signal due to the fact that the two light sources with respective different polarization are not perfectly equal.

The width of the signal peaks, however, depends on the optical system of the measuring device and is independent of the measurement object surface type. Thus, the position of the surface can be found by searching for a signal peak of known width. The surface is therefore preferably calculated by searching for a signal peak of this width. The surface is then located at the position of maximum or minimum intensity of such a peak.

According to the invention, an optical system and an associated method are provided for generating a pattern for a confocal microscope that changes over time in which a movement of the projector pattern is simplified.

The invention claimed is:

1. An optical system for generating a pattern that changes over time for a confocal microscope, the optical system comprising:
   a light source arrangement from which a light beam travels to an object that reflects the light beam to generate a reflected light beam;
   a beam splitter for allowing passage of the light beam proceeding from the light source arrangement in the direction of the object and for deflecting the reflected light beam, reflected by the object in a focal plane, in the direction of a detector, wherein the detector includes a detector pattern for detecting an image of the object; and
   a lens arrangement between the beam splitter and the object,
   wherein the light source arrangement includes:
      a light source that generates the light beam, and
      a device configured to switch a direction of polarization of the light beam to generate a changing projector pattern.

2. The optical system according to claim 1, wherein the device is fixedly downstream and is a controllable optical retarder.

3. The optical system according to claim 2, wherein the controllable optical retarder is a Pockels cell configured to rotate a direction of polarization from entrance to exit depending on a voltage applied to electric terminals of the Pockels cell,
   wherein the Pockels cell is configured such that changing the voltage applied to the electric terminals from a first voltage to a second voltage changes a retardation by lambda/2 or an odd multiple thereof.

4. The optical system according to claim 2, wherein the controllable optical retarder is a stationary rotating lambda/4 retarder.

5. The optical system according to claim 1, wherein the light source is a laser diode that emits polarized light or an LED having a downstream polarizer.

6. The optical system according to claim 1, wherein the projector pattern is a line pattern or a checkerboard pattern.

7. The optical system according to claim 1, further comprising:
   means for aligning the projector pattern and the detector pattern.

8. The optical system according to claim 1, further comprising:
   a transparent LCD configured to generate the projector pattern.

9. The optical system according to claim 1, wherein a filter is provided as a means for evaluating received signals, and
   wherein a switching frequency of the filter is synchronized with a switching frequency for a polarization direction of the light source.

10. The optical system according to claim 9, wherein the filter is a lock-in amplifier.

11. A method for scanning a surface of an object using the optical system according to any of claims 1-4, 5, and 6-10, the method comprising the steps of:
   aligning the projector pattern and the detector pattern;
   tuning the focal plane during a change of the projector pattern with a high switching frequency;
   receiving a signal having a frequency corresponding to the switching frequency;
   narrow-band filtering of the received signal and searching for a maximum intensity of the signal after the narrow band filtering; and
   searching for a signal peak of constant width.

12. An optical system for generating a pattern that changes over time for a confocal microscope, the optical system comprising:
   a light source arrangement configured to emit a light beam,
      wherein the light source arrangement includes a first light source and a second light source,
      wherein a polarization direction of light emitted from the first light source is rotated 90° with respect to a polarization direction of light emitted from the second light source, and
      wherein a light path of the first light source and a light path of the second light source are combined into an optical beam path within the light source arrangement;
   a beam splitter for allowing passage of the light beam emitted from the light source arrangement in a direction of an object and for deflecting a reflected light beam, reflected by the object in a focal plane, in the direction of a detector,
   wherein the detector includes a detector pattern for detecting an image of the object; and
   a lens arrangement between the beam splitter and the object,
   wherein the light source arrangement includes a switching device configured to switch a polarization of the light beam emitted from the light source arrangement by alternately switching the first light source and the second light source to a switched-on state such that only one of the first light source and the second light source is in a switched-on state at a time.

13. The optical system according to claim 12, wherein the first light source and the second light source are arranged side by side.

14. The optical system according to claim 13, further comprising:
   a diffusion disk downstream of the first light source and the second light source.

15. The optical system according to claim 13, further comprising:
   a beam combiner,
   wherein the first light source and the second light source are arranged offset by 90°, and the beam combiner is arranged to combine the light path of the first light source and the light path of the second light source into the optical beam path combining their light paths into the single light path.

16. The optical system according to claim 12, wherein the light emitted from the first light source and the light emitted from the second light source are linearly polarized.

17. The optical system according to claim 16, further comprising:
   wherein a lambda/4 retarder is arranged downstream from the light source arrangement and configured to convert the polarization directions into two circular polarization directions, one counterclockwise and one clockwise.

18. The optical system according to claim 17, further comprising:
   a linear polarizer configured to block light from positions at which the polarization is rotated 90°, and allow light to pass through from positions at which the polarization direction is present so that the projector pattern is transparent at these positions, wherein the linear polarizer is arranged between a structured retarder of the lambda/4 retarder and the lens arrangement.

* * * * *